United States Patent
San et al.

(10) Patent No.: US 9,562,224 B2
(45) Date of Patent: Feb. 7, 2017

(54) **REDUCED ACTIVITY OF *UBICA* IN *E. COLI***

(75) Inventors: Ka-Yiu San, Houston, TX (US); George Bennett, Houston, TX (US)

(73) Assignee: William Marsh Rice University, Houston, TX (US)

( * ) Notice: Subject to any disclaimer, the term of this patent is extended or adjusted under 35 U.S.C. 154(b) by 2279 days.

(21) Appl. No.: 12/439,504

(22) PCT Filed: Sep. 7, 2007

(86) PCT No.: PCT/US2007/077947
§ 371 (c)(1),
(2), (4) Date: Feb. 27, 2009

(87) PCT Pub. No.: WO2008/097353
PCT Pub. Date: Aug. 14, 2008

(65) Prior Publication Data
US 2010/0009403 A1 Jan. 14, 2010

Related U.S. Application Data

(60) Provisional application No. 60/824,879, filed on Sep. 7, 2006.

(51) Int. Cl.
| | |
|---|---|
| *C12N 1/20* | (2006.01) |
| *C12N 15/00* | (2006.01) |
| *C12N 9/00* | (2006.01) |
| *C12N 9/02* | (2006.01) |
| *C12N 9/04* | (2006.01) |
| *C12P 7/00* | (2006.01) |
| *C12N 9/88* | (2006.01) |
| *C12N 9/10* | (2006.01) |
| *C12P 1/04* | (2006.01) |

(52) U.S. Cl.
CPC . *C12N 9/88* (2013.01); *C12N 1/20* (2013.01); *C12N 9/1085* (2013.01); *C12P 1/04* (2013.01); *Y02P 20/52* (2015.11)

(58) Field of Classification Search
None
See application file for complete search history.

(56) References Cited

U.S. PATENT DOCUMENTS

2002/0160461 A1* 10/2002 Nakai et al. .................... 435/89

OTHER PUBLICATIONS

Wu et al. Mutants of *Escherichia coli* affected in respiration: the cloning and nucleotide sequence of ubiA, encoding the membrane-bound p-hydroxybenzoate:octaprenyltransferase. Gen Microbiol. Aug. 1993;139(8):1795-805.*
Becker et al. Regulatory O2 tensions for the synthesis of fermentation products in *Escherichia coli* and relation to aerobic respiration. Arch Microbiol. Oct. 1997;168(4):290-6.*
Yang et al. Effect of inactivation of nuo and ackA-pta on redistribution of metabolic fluxes in *Escherichia coli*. Yang YT, Bennett GN, San KY. Biotechnol Bioeng. Nov. 5, 1999;65(3):291-7.*
Kwon et al. Regulation of the ubiquinone (coenzyme Q) biosynthetic genes ubiCA in *Escherichia coli*. Curr Microbiol. Apr. 2005;50(4):180-9. Epub Mar. 15, 2005.*
PCT/US07/77947, Jul. 25, 2008, Rice University, Search Report.
Calhoon, M.W., et al., Energetic efficiency of *Escherichia coli*: effects of mutations in components of the aerobic respiratory chain. J. Bacteriol. 175:3020-3025 (1993).
Ingledew, W.J. et al., the respiratory chains of *Escherichia coli*. Microbiol. Rev. 48:222-71 (1984).
Korshunov, S., et al., Detection and Quantification of Superoxide Formed within the Periplasm of *Escherichia coli*: Journal of Bacteriology 188:6326-6334 (2006).
Soballe, B., et al., Requirement for ubiquinone downstream of cytochrome(s) b in the oxygen-terminated respiratory chains of *Eschericia coli* K-12 revealed using a null mutant allele of *ubiCA*. Microbiology 144:361-373 (1998).
Zhu, X., et al., Production of Ubiquinone in *Escherichia coli* by Expression of Various Genes Responsible for Ubiquinone Biosynthesis: J. Fermentation and Bioengineering. 79:493-495 (1995).

* cited by examiner

*Primary Examiner* — Yong Pak
(74) *Attorney, Agent, or Firm* — Boulware & Valoir

(57) ABSTRACT

Production of products by engineered bacteria is increased by regulating cellular respiration. Cellular respiration is controlled by reducing electron transfer enzyme activity. Some examples of electron transfer enzymes include NADH dehydrogenases, Succinate dehydrogenases, ubiquinone synthesis, cytochrome O, and cytochrome D. In one example, deletion of UbiCA prevents respiration. Respiration can the be controlled by addition of ubiquinone or expression of ubiCA.

7 Claims, 1 Drawing Sheet

REDUCED ACTIVITY OF UBICA IN E. COLI

CROSS-REFERENCE TO RELATED APPLICATIONS

This application is a 35 U.S.C. Section 371 of PCT/US2007/077947 filed Sep. 7, 2007, which claims priority to U.S. Provisional Application 60/824,879 filed Sep. 7, 2006, both incorporated by reference in their entirety.

FEDERALLY SPONSORED RESEARCH STATEMENT

This invention was made with government support under Grant No. BES-0222691 awarded by the National Science Foundation. The government has certain rights in the invention.

REFERENCE TO MICROFICHE APPENDIX

Not applicable.

FIELD OF THE INVENTION

The invention relates to increased production of products by engineered bacteria by limiting respiration, thus conserving carbon for production even in the presence of excess oxygen. Specifically, the invention relates to a ΔubiCA bacteria and its uses.

BACKGROUND OF THE INVENTION

The energetic state of microbial cells is very important during cell growth and product production. Currently, significant numbers of valuable products are produced through anaerobic fermentation. However, productivity, mainly production rate, of these processes is usually hampered by slow cell growth and low culture density. This is because under anaerobic conditions the cell generates much less energy from the nutrient; it mostly derives its energy through glycolysis that only yields two moles of ATP per mole of glucose consumed. This ATP yield is much lower than that of aerobic respiration, however, the remaining carbon is conserved for product formation. Certainly, a higher energy yield through aerobic respiration can be achieved, but only at the expense of releasing carbon atoms stored in the feedstock (hence lower product yields).

The aerobic respiratory chain of *Escherichia coli* (*E. coli*) is composed of a number of membrane-bound, multisubunit enzymes located within the cytoplasmic membrane. Dehydrogenases such as NADH dehydrogenase or succinate dehydrogenase reduce ubiquinone to ubiquinol within the cytoplasmic membrane. Ubiquinol diffuses within the membrane bilayer and is oxidized by either of two quinol oxidase complexes: the cytochrome O complex or the cytochrome D complex. For a complete review of *E. coli* respiration, see Ingledew and Poole (1984) incorporated herein by reference.

Two operating procedures have been developed in an attempt to strike an ideal balance between energy generation through aerobic respiration (for better cell growth and cell "fitness") and carbon conservation. One approach is to operate the bioreactor under microaerobic conditions. This reactor configuration provides a slight increase in ATP supply and limits the amount of carbon lost during aerobic respiration. However, it is technically difficult to maintain a constant microaerobic environment in real processes, especially for large bioreactors. Variation in extent of aeration is a problem even in those situations where near complete oxygen saturation is desired. Any increased supply of oxygen will favor cell growth and subsequently decrease the product yield.

A second strategy is to perform the process in two stages. The first stage is to grow the cell under aerobic conditions and then switch to anaerobic conditions for product formation. This strategy avoids the possibility of oxygen oversupply and guarantees a certain product yield for the second stage. However, the supply of ATP still is low during the product formation stage. There are also biological complexities that arise during the transition (proper synthesis and activation of required proteins and cofactors, triggering of cellular stress responses).

What is required to improve production in engineered bacterial cells is a balance between energy generation through aerobic respiration and carbon atom conservation by limited respiration. By limiting respiration, the cell will not "waste" carbon atoms even when the oxygen supply is abundant. At the same time, a sufficient supply of ATP will be available for cell growth and product formation throughout the fermentation processes. Strain respiration can be maintained at levels required for specific bioproduction needs, thus optimizing respiration and carbon conservation.

SUMMARY OF THE INVENTION

The Invention is generally directed to engineered bacterial cells having a balance between energy generation through aerobic respiration and carbon atom conservation by limited respiration. Disruption, mutation, inactivation, or complete deletion of electron transfer genes can be used to control respiration. The invention improves the performance of anaerobic processes, particularly those processes requiring significant energy for substrate uptake, product formation, or processes that do not perform well due to a lack of electron acceptors.

In one embodiment, ATP is limited through control of aerobic respiration. This approach provides a limited carbon flow for energy generation independent of oxygen supply; thus this approach also conserves substrate carbon atoms for product formation (hence be able to maintain high product yield). Aerobic respiration can be limited in two ways:
1. Introducing a disruption in a step involved in the normal electron transfer chain.
2. Express the gene involved in electron transfer at a controlled or reduced level For example, the invention can be achieved by reducing activity of one or more NDH, SDH, UbiCA, CytO, or CytD. In one embodiment, ubiCA is deleted, and in another embodiment a mutant ubiCA with reduced activity is expressed. Deletion of the ubiCA operon prevents production of ubiquinone. Electron transfer can then be regulated by adding ubiquinone or controlling exogenous ubiCA expression.

DESCRIPTION OF EMBODIMENTS OF THE INVENTION

Figure 1:
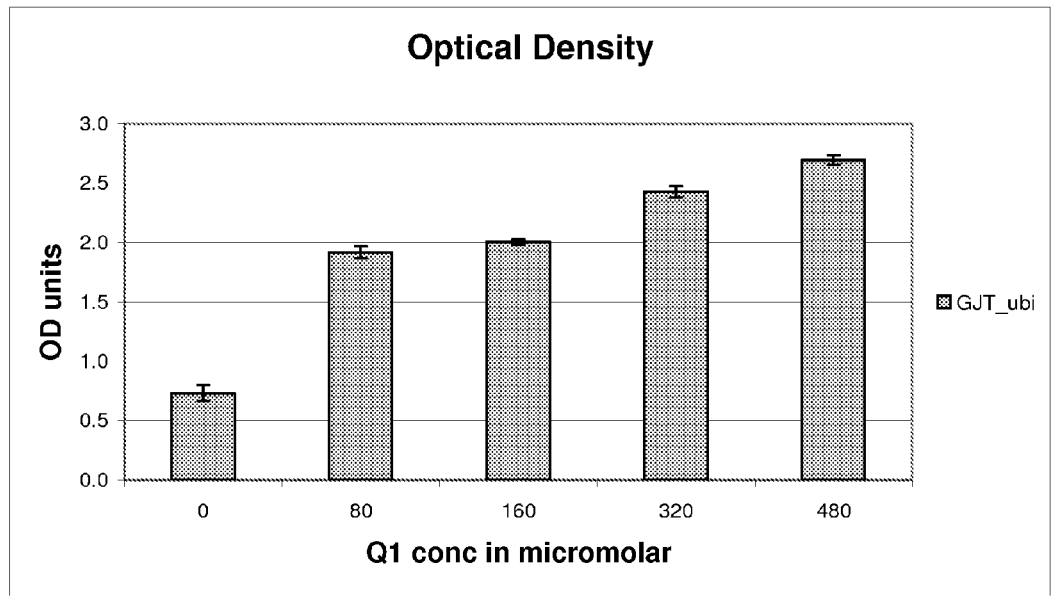
FIG. 1: Optical density

Ubiquinone (Coenzyme Q) is an essential component of bacterial respiratory chains. The first committed step in the biosynthetic pathway is the formation of 4-hydroxybenzoate from chorismate by the enzyme chorismate pyruvate-lyase encoded by the ubiC gene. The 4-hydroxybenzoate is prenylated by 4-hydroxybenzoate octaprenyltransferase encoded by the ubiA gene. The two genes are linked at 91.5 min in the *E. coli* chromosome (see e.g, AP_004540 and AP_004541), and are found in all bacterial species with homologies ranging from to as low as 33% (while still being recognized as chorismate-pyruvate lyase, see e.g., NP_932913) and 24% (while still being recognized as polyprenyltransferase, see e.g., ZP_00987621).

NADH-CoQ reductase in *E. coli* is encoded by either of two different membrane-bound NADH dehydrogenases (NDH-1 and NDH-2). Succinate dehydrogenase (SDH) reduces succinate to fumarate and reduces ubiquinone to ubiquinol. The Cyto complex is encoded by cyoABCDE operon and Cytd encoded by the cydAB operon.

Carboxylic acids described herein can be a salt, acid, base, or derivative depending on structure, pH, and ions present. For example, the terms "succinate" and "succinic acid" are used interchangeably herein. Chemicals used herein, including formate, glyoxylate, lactate, malate, oxaloacetate (OAA), phosphoenolpyruvate (PEP), and pyruvate, can be found in the NATIONAL LIBRARY OF MEDICINE® PUBCHEM™ database (pubchem.ncbi.nlm.nih.gov) incorporated herein by reference Bacterial metabolic pathways including the Krebs cycle (also called citric acid, tricarboxylic acid, or TCA cycle) can be found in *Principles of Biochemistry* $2^{nd}$ ed., by Lehninger (1993), incorporated herein by reference, as well as other biochemistry texts.

The terms "operably associated" or "operably linked," as used herein, refer to functionally coupled nucleic acid sequences.

"Reduced activity" is defined herein to be at least a 75% reduction in protein activity, as compared with an appropriate control species. Preferably, at least 80, 85, 90, or 95% reduction in activity is attained, and in the most preferred embodiment, the activity is eliminated (100% or "inactivation"). Proteins can be inactivated with inhibitors, by mutation, or by suppression of expression or translation, and the like. By "null mutant" or "null mutation" what is meant is that protein activity is completely inactivated. In one example, the control plasmid is inserted without the gene of interest. In another example, the gene of interest is completely removed by recombination. Additionally, the gene of interest may be removed by inactivation, mutation, or truncation which eliminates activity.

"Overexpression" or "overexpressed" is defined herein to be greater than wild type activity, preferably above 125% increase, more preferably above 150% increase in protein activity as compared with an appropriate control species. Preferably, the activity is increased 100-500%. Overexpression is achieved by mutating the protein to produce a more active form, a more stable form, or a form that is resistant to inhibition, by removing inhibitors, adding activators, and the like. Overexpression can also be achieved by removing repressors, adding multiple copies of a gene to the cell, up-regulating an existing gene, adding an exogenous gene, and the like.

The terms "disruption" and "disruption strains," as used herein, refer to cell strains in which the native gene is mutated, deleted, interrupted, or down-regulated in such a way as to decrease the activity of the gene. A gene is completely (100%) reduced by knockout or removal of a portion or the entire gene sequence. Use of a frame shift mutation, early stop codon, point mutations of critical residues, or deletions or insertions, and the like, can completely inactivate (100%) gene product by completely preventing transcription and/or translation of active protein.

The term "exogenous" indicates that the protein or nucleic acid is a non-native molecule introduced from outside the organism or system without regard to species of origin. For example, an exogenous peptide may be applied to the cell culture; an exogenous RNA may be expressed from a recombinant DNA transfected into a cell; or a native gene may be under the control of exogenous regulatory sequences.

As used herein "recombinant" is relating to, derived from, or containing genetically engineered material.

A gene or cDNA may be "optimized" for expression in *E. coli* or other bacterial species using the codon bias for the species. Various nucleotides can encode a single peptide sequence. Understanding the inherent degeneracy of the genetic code allows one of ordinary skill in the art to design multiple nucleotides which encode the same amino acid sequence. NCBI™ provides codon usage databases for optimizing DNA sequences for protein expression in various species.

In calculating "% identity" the unaligned terminal portions of the query sequence are not included in the calculation. The identity is calculated over the entire length of the reference sequence; thus short local alignments with a query sequence are not relevant (e.g., % identity=number of aligned residues in the query sequence/length of reference sequence). Alignments are performed using BLAST homology alignment as described by Tatusova TA & Madden TL (1999) FEMS Microbiol. Lett. 174:247-50. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 11 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W word size [Integer] default=11 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs. This program is available online at NCBI™ (www.ncbi.nlm.nih.gov/BLAST/).

Common restriction enzymes and restriction sites are found at NEB® (New England Biolabs®, www.neb.com) and Invitrogen® (www.invitrogen.com). ATCC®, American Type Culture Collection™ (www.atcc.org) has an extensive collection of cell strains that are publicly available and incorporated herein by reference.

TABLE 1

ABBREVIATIONS

| Abbr | Term |
|---|---|
| CytC | cytochrome C |
| FMN | flavin mononucleotide |
| FRD | fumarate reductase |
| Ap/Ap$^R$ | ampicillin/ampicillin resistance |
| ATCC ® | American Tissue-type Culture Collection |
| CoQ | coenzyme Q or ubiquinone |
| Cm | chloramphenicol |
| Cn | carbenicillin |
| ColE1 | gram-negative origin of replication |
| Em | erythromycin |

TABLE 1-continued

ABBREVIATIONS

| Abbr | Term |
|---|---|
| FAD | flavin adenine dinucleotide |
| GC-MS | gas chromatography-mass spectroscopy |
| ICT | isocitrate |
| Km/Km$^R$ | kanamycin/kanamycin resistance |
| Mal | malate |
| MLS$^R$ | macrolide, lincosamide and streptogramin A resistance |
| Nal | nalidixic acid |
| NCBI ™ | National Center for Biotechnology Information |
| NDH | NADH dehydrogenase |
| OAA | oxaloacetate |
| OriII | gram-positive origin of replication |
| Ox/Ox$^R$ | oxacillin/oxacillin resistance |
| PEP | phosphoenolpyruvate |
| PYR | pyruvate |
| SDH | succinate dehydrogenase |
| Sm/Sm$^R$ | streptomycin/streptomycin resistance |
| Suc | succinate |
| Tc | tetracycline |
| Thi$^R$/Cm$^R$ | thiamphenicol/chloramphenicol resistance |
| wt | wild-type |

Plasmids and strains used in certain embodiments of the invention are set forth in Table 2.

TABLE 2

PLASMIDS AND STRAINS

| Plasmid/Strain | Genotype | Ref |
|---|---|---|
| pDHK29 | Cloning vector Cm$^R$ | Phillips, 2000 |
| pTrc99A | Cloning vector Ap$^R$ | PHARMACIA ® |
| pTrcHisTOPO | Expression vector w/Trc promoter, His Tag | INVITROGEN ® |
| pUBICA | pTrcHisTOPO w/ubiCA | This work |
| MG1655 | Wild type (F-λ-) | Guyer, 1988 |
| AMS001 | ΔubiCA | This work |
| UbiCA | AMS001 (pUBICA) | This work |

When plasmids are used, the effect of host/plasmid interaction is minimized by comparing three different systems consisting of: the host only, a plasmid expressing biologically active enzyme, and a control system with the expression vector alone.

EXAMPLE 1

Limiting UQ-1

We sought to study the effect of exogenous supplementation of ubiquinone-1 (UQ-1) to a ΔubiCA mutant strain, AMS001 on cell respiration by measuring both cell growth and lactate yield, as an example of product formation. This mutant cannot produce ubiquinone due to a disruption (deletion) in ubiCA.

Figure 2:
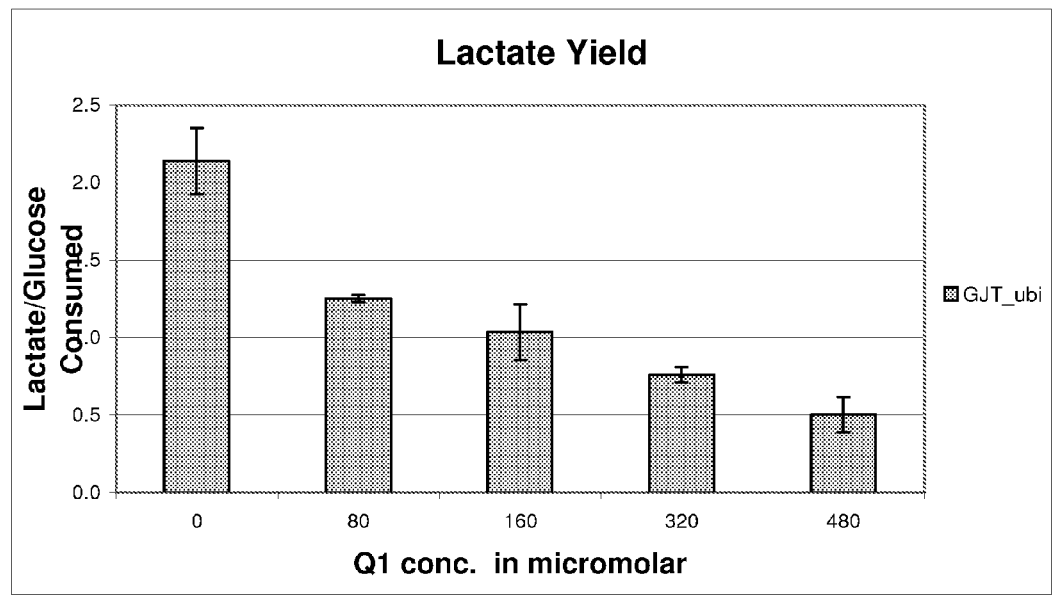
FIG. 2: Lactate Yield

Aerobic shake flask experiments with this mutant strain were carried out in 125-ml shake flasks containing 10 ml of LB medium supplemented with 20 g/L of glucose in a rotary shaker at 37° C. and 250 rpm. The final optical density and the specific lactate yield after 24 hours are summarized in FIGS. 1 and 2.

The ΔubiCA mutant strain grows very poorly and produces a large amount of lactate. The ΔubiCA mutant, due to the disruption in the electron chain, cannot use oxygen as the electron receptor even grown under aerobic conditions. Instead, the cell opted to recycle the NADH to NAD+ through the formation of lactate (the ethanol pathway is not active aerobically). Thus, the metabolic pattern of the ΔubiCA mutant strain behaves similar to one that is grown anaerobically, even in the presence of air.

Addition of different amounts of ubiquinone to the culture increased the final optical density and reduced the amount of lactate accumulated. The mutant strain responded to ubiquinone supplementation in a graded manner. The reduction in lactate formation suggests that the electron transfer chain is partially recovered and the cells are capable using oxygen as the electron acceptor. However, the mutant strain did not fully recover even when the concentration was increased to 400 µM. It is possible that the low solubility of UQ-1 in the medium limits the uptake of this molecule. Another explanation might be that some intermediate products in the ubiquinone biosynthesis pathway are necessary for full recovery and restoration of the cell. These experiments demonstrate recovery by the exogenous addition of ubiquinone and control of cellular respiration rates using ubiquinone supplementation.

EXAMPLE 2

Expression of UbiCA

Complementation experiments were performed by transforming AMS001 with pUBICA. The growth characteristics and metabolic patterns were fully recovered by the introduction of a plasmid carrying a normal ubiCA gene to the ΔubiCA mutant (data not shown). Expression of exogenous UbiCA demonstrates influence of growth behavior and metabolic patterns in an aerobic E. coli culture by manipulating the supply of the ubiquinone. By manipulating expression of the ubiCA operon, the amount of ubiquinone can be controlled and respiration can be tailored to the production process.

REFERENCES

All references are listed herein for the convenience of the reader. Each is incorporated by reference in its entirety.
1. Calhoun, et al., "Energetic efficiency of Escherichia coli: effects of mutations in components of the aerobic respiratory chain." J. Bacteriol. 175:3020-25 (1993).
2. Ingledew and Poole, "The Respiratory Chains of Escherichia coli." Microbiol. Rev. 48:222-71 (1984).
3. Quarino, et al., "An ELISA method for the identification of salivary amylase." J Forensic Sc. (4): 973-6 (2005).
4. Aluoch, et al., "Development of an oral biosensor for salivary amylase using a monodispersed silver for signal amplification." Anal Biochem. 240(1): 136-44 (2005).

What is claimed is:

1. An engineered bacterial cell comprising:
   a) a disruption in the ubiCA operon, and
   b) a vector comprising controlled expression of an exogenous ubiCA gene.

2. The engineered bacterial cell of claim 1, further comprising reduced activity of an electron transfer enzyme selected from the group consisting of NADH dehydrogenase (NDH), Succinate dehydrogenase (SDH), Cytochrome O (Cyto), Cytochrome D (Cytd), and combinations thereof.

3. The engineered bacterial cell of claim 2, wherein said cell has a deletion of one or more genes selected from the group consisting of ndh-1, ndh-2, sdh, cyoA, cyoB, cyoC, cyoD, cydA, cydB, and combinations thereof.

4. A method of increasing product yield in an engineered bacterial cell comprising:

a) culturing the engineered bacterial cell of claim 1;
b) regulating electron transfer activity by addition of ubiquinone or by manipulating expression of said exogenous ubiCA gene; and
c) isolating a product from said cell.

5. The method of claim 4, wherein said cell has a deletion of one or more genes selected from the group consisting of ndh-1, ndh-2, sdh, cyoA, cyoB, cyoC, cyoD, cydA, cydB, and combinations thereof.

6. An engineered bacterial cell comprising:
a) a disruption in a ubiA gene, a UbiC gene, or combinations thereof, and
b) a vector allowing controllable expression of an added exogenous ubiCA gene.

7. A method of increasing product yield in an engineered bacterial cell comprising:
a) culturing the engineered bacterial cell of claim 6;
b) regulating electron transfer activity in said cell by addition of ubiquinone or by manipulating expression of said added exogenous ubiCA gene; and
c) isolating a product from said cells.

* * * * *